United States Patent [19]

Tayler et al.

[11] Patent Number: 5,470,869
[45] Date of Patent: Nov. 28, 1995

[54] PYRAZOLIUM FUNGICIDAL COMPOSITIONS

[75] Inventors: Peter N. Tayler, Stubbington, England; Lynn S. Evans, Langhorne, Pa.

[73] Assignee: American Cyanamid Company, Wayne, N.J.

[21] Appl. No.: 189,380

[22] Filed: Jan. 31, 1994

[51] Int. Cl.$^6$ .................................................. A01N 43/56
[52] U.S. Cl. .................................................. 514/406
[58] Field of Search .................................................. 514/406

[56] References Cited

U.S. PATENT DOCUMENTS

| | | | |
|---|---|---|---|
| 3,492,402 | 1/1970 | Baker et al. | 424/186 |
| 3,930,011 | 12/1975 | Walworth | 514/406 |
| 4,782,074 | 11/1988 | Spatz | 514/406 |
| 4,877,441 | 10/1989 | Mari et al. | 514/406 |

OTHER PUBLICATIONS

De Baynast et al, C. A., vol. 74 (1971) 52492j.

Giltrap, C. A.; vol. 105, (1986) 105: 129311t.

*Primary Examiner*—Allen J. Robinson
*Attorney, Agent, or Firm*—Gregory M. Hill

[57] ABSTRACT

The present invention provides compositions comprising pyrazolium compounds and methods for using those compositions as fungicides.

23 Claims, No Drawings

PYRAZOLIUM FUNGICIDAL COMPOSITIONS

BACKGROUND OF THE INVENTION

Pyrazolium compounds are known to possess biological activity. U.S. Pat. No. 3,930,011 describes pyrazolium fungicides and certain compositions containing them. That patent teaches that the pyrazolium fungicides are applied at rates of from about 0.5 kg/ha to 10.0 kg/ha. However, certain fungicidal compositions containing pyrazolium compounds are unacceptably phytotoxic at the application rates required to prevent or control fungal infestation and disease.

It is therefore an object of the present invention to provide more effective and less phytotoxic pyrazolium fungicidal compositions.

It is also an object of the present invention to provide a more effective method for preventing, controlling or ameliorating a disease caused by a phytopathogenic fungus.

It is a further object of the present invention to provide a more effective and less phytotoxic method for protecting a crop, crop seed or tuber from fungal infestation and disease.

These and other objects of the present invention will become more apparent from the detailed description thereof set forth below.

SUMMARY OF THE INVENTION

The present invention provides a composition for controlling phytopathogenic fungi which comprises a fungicidally effective amount of a pyrazolium compound and oil.

The present invention also provides methods for using that composition to prevent, control or ameliorate a disease caused by a phytopathogenic fungus and to protect a crop, crop seed or tuber from fungal infestation and disease.

DETAILED DESCRIPTION OF THE INVENTION

Phytopathogenic fungi are the causal agents for many diseases that infect and destroy crops. In the United States alone, crops must compete with about 18,000 species of fungi. Accordingly, there is a need for new and more effective fungicidal compositions for preventing or controlling the vast array of fungal infestations of crops.

Surprisingly, it has now been found that the fungicidal activity of pyrazolium compounds is enhanced to a significant extent by the co-application of oils. That enhanced activity permits the use of lower amounts of active ingredient thereby reducing phytotoxicity.

Advantageously, the present invention provides a composition for controlling phytopathogenic fungi which comprises a fungicidally effective amount of a pyrazolium compound having the following structural formula I

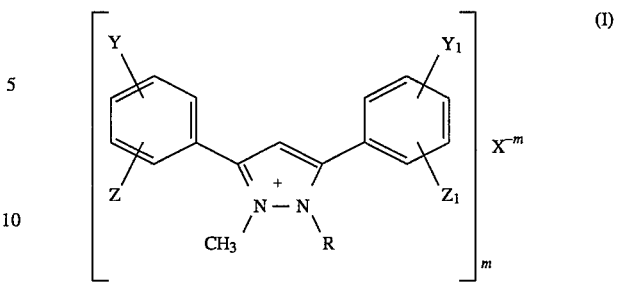

wherein
R is $C_1$–$C_3$alkyl, allyl, propynyl, ethylcarboxymethyl, phenyl or benzyl;
Y, $Y_1$, z and $Z_1$ each independently hydrogen, halogen, $C_1$–$C_4$alkyl or $C_1$–$C_4$alkoxy;
X is an anion having a charge of 1 or 2; and
m is an integer of 1 or 2, and oil.

The present invention also provides a method for the prevention, control or amelioration of a disease caused by a phytopathogenic fungus which comprises contacting said fungus with a fungicidally effective amount of a composition which comprises a pyrazolium compound of formula I and oil.

The present invention further provides a method for the protection of a crop, crop seed or tuber from fungal infestation and disease which comprises applying to the crop, crop seed or tuber, or to the medium or water in which it is growing, a fungicidally effective amount of a composition which comprises a pyrazolium compound of formula I and oil.

The term "medium" used herein is defined as any environment, including but not limited to artificial nutrients, hydroponics or soil, in which a crop can be kept, live or thrive.

Oils suitable for use in the compositions and methods of this invention comprise agronomically acceptable oils and include mineral oils such as refined mineral oils, highly refined mineral oils, refined paraffinic oils and highly refined paraffinic oils; vegetable oils such as alkylated vegetable oils, seed oils, nut oils and alkylated seed oils; animal oils such as fish oils, fish-liver oils and sperm oil; and mixtures thereof. Preferred oils include alkylated vegetable oils such as methylated vegetable oils and alkylated seed oils such as methylated seed oils.

Many of the oils are commercially available as adjuvants under a variety of tradenames. Oil containing adjuvants which are particularly suitable for use in the compositions and methods of this invention include ACTIPRON® (British Petroleum), ATLAS-ADHERBE® (Atlas Chemical Industries), ATPLUS 412® (ICI Surfactants), ATPLUS 419® (ICI Surfactants), QUADRANGLE CROPSPRAY IIE® (Quadrangle), DYNE-AMIC® (Helena Chemical Co.), SCS 2660® (ICI Surfactants), SUN-IT II® (AGSCO, Inc.) and SCOIL® (AGSCO, Inc.), among others with ACTIPRON® being preferred.

Surprisingly, it has been discovered that oil containing adjuvants, in general, stand apart from other adjuvants in their ability to increase the fungicidal activity of formula I pyrazolium compounds without causing a significant increase in phytotoxicity.

Preferred formula I pyrazolium compounds suitable for use in the compositions and methods of this invention are those wherein
R is methyl;
Y, $Y_1$, Z and $Z_1$ are each independently hydrogen, Cl, F, I, methyl, methoxy or butoxy;

X is an anion having a charge of 1 or 2; and m is an integer of 1 or 2.

A most preferred formula I pyrazolium compound is 1,2-dimethyl-3,5-diphenylpyrazolium methyl sulfate.

The pyrazolium fungicidal compositions of the present invention are especially useful for controlling or preventing the growth of phytopathogenic fungi such as *Erysiphe graminis* f.sp. tritici, *Erysiphe graminis* f.sp. hordei and *Leptosphaeria nodorum*. Therefore, harmful diseases such as wheat powdery mildew, barley powdery mildew and wheat *Septoria nodorum* leaf blotch may be prevented or controlled.

Crops, especially cereal crops such as wheat, barley, oat and rice, may be protected from fungal infestation and disease by spraying the crops with a composition, preferably an aqueous composition, containing a formula I pyrazolium compound and oil. The composition should contain an effective amount of the pyrazolium compound and an effective amount of the oil. The effective amount will vary depending upon factors such as the crop, the virulence of the target fungus, the environment of the treatment and other ambient conditions. Typical rates of application for the formula I pyrazolium compound are about 0.05 kg/ha to 0.5 kg/ha, preferably 0.15 kg/ha to 0.4.5 kg/ha, and typical rates of application for the oil are about 0.1 L/ha to 4.0 L/ha, preferably about 0.2 L/ha to 2.0 L/ha. Those application rates may be readily achieved by applying from about 100 L/ha to 500 L/ha, preferably about 150 L/ha to 250 L/ha, of the aqueous fungicidal composition to the crops.

The compositions of the present invention may be prepared as aqueous compositions by mixing an oil with a separate composition containing a formula I pyrazolium compound in water ill a tank. The aqueous compositions typically contain about 0.05% vol/vol to 4.0% vol/vol of the oil, about 0.038% wt/vol to 0.45% wt/vol of the formula I pyrazolium compound and water. Alternatively, an aqueous composition may be prepared by mixing a premixed concentrate composition comprising both oil and a formula I pyrazolium compound with water in a tank. Such a concentrate composition typically comprises about 12.5% vol/vol to 28.6% vol/vol of the oil, about 3.2% wt/vol to 9.5% wt/vol of the formula I pyrazolium compound and an aqueous carrier.

Preferred aqueous compositions of this invention are those comprising about 0.1% wt/vol to 0.25% wt/vol of a formula I pyrazolium compound, about 0.25% vol/vol to 0.5% vol/vol of oil, and water.

Preferred concentrate compositions of this invention are those comprising about 6.7% wt/vol to 8.0% wt/vol of a formula I pyrazolium compound, about 20% vol/vol to 22.2% vol/vol of oil, and an inert carrier.

The compositions of the present invention such as the aqueous compositions and the concentrate compositions may contain one or more additional components such as antifoaming agents, dispersing agents, surfactants, urea, and water.

Application of the compositions of the present invention to the plant, crop, crop seed, tuber or to the medium or water in which it is growing may be accomplished by any of the well known methods in the art including spray, aerosol, atomizer and nebulizer.

Advantageously, other biological chemicals, preferably other fungicides, may be used in conjunction with or in combination with the pyrazolium fungicidal compositions of the present invention.

In order to facilitate a further understanding of the invention, the following examples are presented primarily for the purpose of illustrating more specific details thereof. The invention should not be deemed limited thereby except as defined in the claims.

EXAMPLE 1

Preparation of pyrazolium fungicidal compositions

An aqueous fungicidal composition of the present invention is prepared by admixing 10 mL of a composition containing 21.7% wt/vol 1,2-dimethyl-3,5-diphenylpyrazolium methyl sulfate and water with 10 mL of an adjuvant containing 97% wt/wt refined mineral oil (ACTIPRON®, British Petroleum) in 980 mL of water in a tank to make 1 L of spray solution. The resultant fungicidal composition is identified as composition 1 in Table I.

Using essentially the same procedure, but substituting the appropriate oil containing adjuvant for ACTIPRON®, the aqueous fungicidal compositions identified as compositions 2–4 in Table I are obtained.

TABLE I

| | Aqueous Fungicidal Compositions | | |
|---|---|---|---|
| | Ingredient (% wt/vol) | | |
| Composition | 1,2-Dimethyl-3,5-diphenylpyrazolium methyl sulfate | Oil Containing Adjuvant | Water |
| 1 | 0.217 | ACTIPRON ®/ 1.0 | to 100% |
| 2 | 0.217 | ACTIPRON ®/ 2.0 | to 100% |
| 3 | 0.217 | SUN-IT II ®/ 1.0 | to 100% |
| 4 | 0.217 | QUADRANGLE CROPSPRAY IIE ®/ 1.0 | to 100% |

EXAMPLE 2

Evaluation of fungicidal compositions against wheat powdery mildew

Field plots of winter wheat plants, cv Appollo, at growth stage Z 50–51, with active powdery mildew present, are individually sprayed with one of the compositions listed in Table II. The compositions are sprayed onto the plots at a rate of 200 L/ha and 400 L/ha to provide the equivalent of 0.3 kg/ha and 0.6 kg/ha of 1,2-dimethyl-3,5-diphenylpyrazolium methyl sulfate, from 2.0 L/ha to 8.0 L/ha of the oil containing adjuvant and from 0.2 L/ha to 2.0 L/ha of the non-oil component. The wheat plants are evaluated for crop discoloration 7–10 days after treatment and for disease control two weeks after treatment according to the rating systems shown below. The results of the tests are summarized in Table III.

The compositions listed in Table II are prepared according to the procedure described in Example 1.

Crop Discoloration Rating Scale

Results of crop discoloration evaluations are expressed on a rating scale (0–9). The scale is based upon a visual observation of the severity of plant chlorosis and the proportion of the plant area affected.

| Rating | Meaning |
| --- | --- |
| 0.0 | untreated base line |
| 0.5 | very slight yellowing |
| 1.0 | yellowing just visible from 50 yards |
| 1.5 | yellowing clearly visible from 50 yards |
| 2.0 | moderate discoloration |
| 2.5 | moderate to severe discoloration |
| 3.0 | limit of acceptable discoloration |
| 4.0–8.0 | increasing levels of unacceptable discoloration |
| 9.0 | 100% discoloration |

Fungicidal Rating Scale

Results of fungicidal evaluations are expressed as percent disease control according to the following formula.

$$\% \text{ Disease Control} = 100 - \left[ \frac{\% \text{ leaf infected (treated)}}{\% \text{ leaf infected (untreated)}} \times 100 \right]$$

TABLE II

Fungicidal Compositions

Ingredient (% wt/vol)

| Composition | 1,2-Dimethyl-3,5-diphenylpyrazolium methyl sulfate | Oil Containing Adjuvant | Non-Oil Component | Water |
| --- | --- | --- | --- | --- |
| 1 | 0.217 | ACTIPRON ®/ 1.0 | — | to 100% |
| 2 | 0.217 | ACTIPRON ®/ 2.0 | — | to 100% |
| 3 | 0.217 | SUN-IT II ®/ 1.0 | — | to 100% |
| 4 | 0.217 | QUADRANGLE ® CROPSPRAY IIE/1.0 | — | to 100% |
| 5 | 0.217 | — | — | to 100% |
| 6 | 0.217 | — | ¹AGRAL 90 ®/ 0.5 | to 100% |
| 7 | 0.217 | — | ²GALION ®/ 0.1 | to 100% |
| 8 | 0.217 | — | ³TWEEN 20 ®/ 0.5 | to 100% |

¹AGRAL 90 ® - alkyl phenol ethylene oxide condensate, ICI;
²GALION ® - ethylene oxide condensates, Intracrop;
³TWEEN 20 ® sorbitan monoduodeconoate, Atlas Chemical Industries.

TABLE III

Crop Discoloration and Fungicidal Evaluations

| Composition | Rate (L/ha) | Crop Discoloration | % Disease Control |
| --- | --- | --- | --- |
| 1 | 200 | 0.7 | 64 |
|   | 400 | 1.0 | — |
| 2 | 200 | 1.5 | 66 |
|   | 400 | 1.5 | — |
| 3 | 200 | 1.2 | 64 |
|   | 400 | 1.0 | — |
| 4 | 200 | 1.3 | 52 |
|   | 400 | 0.5 | — |
| 5 | 200 | 0.8 | 45 |
|   | 400 | 0.5 | — |
| 6 | 200 | 2.7 | 66 |
|   | 400 | 4.0 | — |
| 7 | 200 | 1.2 | 64 |
|   | 400 | 2.0 | — |
| 8 | 200 | 1.8 | 57 |
|   | 400 | 4.0 | — |

As can be seen from the data in Table III, the compositions of the present invention (compositions 1–4) control wheat powdery mildew more effectively than composition 5 and are significantly less phytotoxic than compositions 6–8.

What is claimed is:

1. A composition for controlling phytopathogenic fungi without causing a significant increase in phytotoxicity which comprises a fungicidally effective amount of a compound having the structural formula

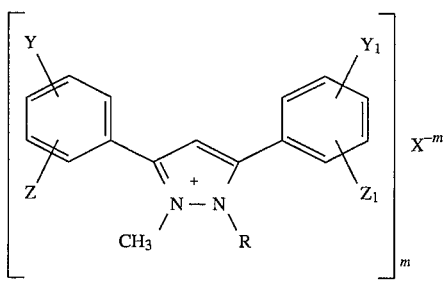

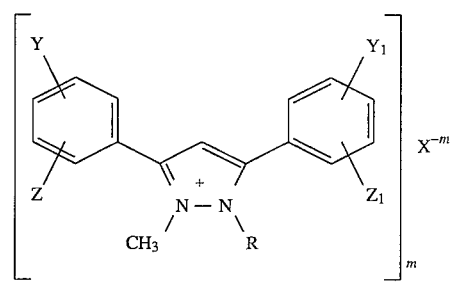

wherein

R is $C_1$-$C_3$alkyl, allyl, propynyl, ethylcarboxymethyl, phenyl or benzyl;

Y, $Y_1$, Z and $Z_1$ are each independently hydrogen, halogen, $C_1$-$C_4$alkyl or $C_1$-$C_4$alkoxy;

X is an anion having a charge of 1 or 2; and m is an integer of 1 or 2, and an enhancing effective amount of an oil selected from the group consisting of a mineral oil, a vegetable oil, an animal oil and mixtures thereof.

2. The composition according to claim 1 wherein the mineral oil is selected from the group consisting of a refined mineral oil, a highly refined mineral oil, a refined paraffinic oil and a highly refined paraffinic oil; and the vegetable oil is selected from the group consisting of an alkylated vegetable oil, a seed oil, a nut oil and an alkylated seed oil.

3. The composition according to claim 1 wherein

R is methyl;

Y, $Y_1$, Z and $Z_1$ are each independently hydrogen, Cl, F, I, methyl, methoxy or butoxy;

X is an anion having a charge of 1 or 2; and m is an integer of 1 or 2.

4. The composition according to claim 3 wherein the compound is 1,2-dimethyl-3,5-diphenylpyrazolium methyl sulfate.

5. The composition according to claim 1 comprising about 3.2% wt/vol to 9.5% wt/vol of the compound, about 12.5% vol/vol to 28.6% vol/vol of the oil, and an aqueous carrier.

6. The composition according to claim 5 which comprises about 6.7% wt/vol to 8.0% wt/vol of the compound and about 20% vol/vol to 22.2% vol/vol of the oil.

7. The composition according to claim 1 comprising about 0.038% wt/vol to 0.45% wt/vol of the compound, about 0.05% vol/vol to 4.0% vol/vol of the oil, and water.

8. The composition according to claim 7 which comprises about 0.1% wt/vol to 0.15% wt/vol of the compound, about 0.25% vol/vol to 0.5% vol/vol of the oil, and water.

9. A method for the control or amelioration of a disease caused by a phytopathogenic fungus without causing a significant increase in phytotoxicity which comprises contacting said fungus with a fungicidally effective amount of a composition which comprises a compound having the structural formula wherein R is $C_1$-$C_3$alkyl, allyl, propynyl, ethylcarboxymethyl, phenyl or benzyl;

Y, $Y_1$, Z and $Z_1$ are each independently hydrogen, halogen, $C_1$-$C_4$alkyl or $C_1$-$C_4$alkoxy;

X is an anion having a charge of 1 or 2; and m is an integer of 1 or 2, and an enhancing effective amount of an oil selected from the group consisting of a mineral oil, a vegetable oil, an animal oil and mixtures thereof.

10. The method according to claim 9 wherein the mineral oil is selected from the group consisting of a refined mineral oil, a highly refined mineral oil, a refined paraffinic oil land a highly refined paraffinic oil; and the vegetable oil is selected from the group consisting of an alkylated vegetable oil, a seed oil, a nut oil and an alkylated seed oil.

11. The method according to claim 9 wherein

R is methyl;

Y, $Y_1$, Z and $Z_1$ are each independently hydrogen, Cl, F, I, methyl, methoxy or butoxy;

X is an anion having a charge of 1 or 2; and m is an integer of 1 or 2.

12. The method according to claim 11 wherein the compound is 1,2-dimethyl-3,5-diphenylpyrazolium methyl sulfate.

13. The method according to claim 9 wherein the disease is selected from the group consisting of wheat powdery mildew, barley powdery mildew and wheat *Septoria nodorum* leaf blotch and the phytopathogenic fungus is selected from the group consisting of *Erysiphe graminis* f.sp. tritici, *Erysiphe graminis* f.sp. hordei and *Leptosphaeria nodorum*.

14. The method according to claim 9 wherein the composition comprises about 0.038% wt/vol to 0.45% wt/vol of the compound, about 0.05% vol/vol to 4.0% vol/vol of the oil, and water.

15. A method for the protection of a crop, crop seed or tuber from fungal infestation and disease which comprises applying to the crop, crop seed or tuber, or to the medium or water in which it is growing, a fungicidally effective amount of a composition which comprises a compound having the structural formula

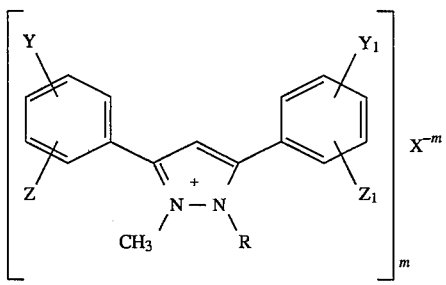

wherein

R is $C_1$-$C_3$alkyl, allyl, propynyl, ethylcarboxymethyl, phenyl or benzyl;

Y, $Y_1$, Z and $Z_1$ are each independently hydrogen, halogen, $C_1$-$C_4$alkyl or $C_1$-$C_4$alkoxy;

X is an anion having a charge of 1 or 2; and m is an integer of 1 or 2, and an enhancing effective amount of an oil selected from the group consisting of a mineral oil, a vegetable oil, an animal oil and mixtures thereof.

16. The method according to claim 15 wherein the mineral oil is selected from the group consisting of a refined mineral oil, a highly refined mineral oil, a refined paraffinic oil and a highly refined paraffinic oil; and the vegetable oil is selected from the group consisting of an alkylated vegetable oil, a seed oil, a nut oil and an alkylated seed oil.

17. The method according to claim 15 wherein

R is methyl;

Y, $Y_1$, Z and $Z_1$ are each independently hydrogen, Cl, F, I, methyl, methoxy or butoxy;

X is an anion having a charge of 1 or 2; and m is an integer of 1 or 2.

18. The method according to claim 17 wherein the compound is 1,2-dimethyl-3,5-diphenylpyrazolium methyl sulfate.

19. The method according to claim 15 wherein the crop is a cereal crop.

20. The method according to claim 19 wherein the cereal crop is selected from the group consisting of wheat, barley, oat and rice.

21. The method according to claim 15 wherein the fungal disease is selected from the group consisting of wheat powdery mildew, barley powdery mildew and wheat *Septoria nodorum* leaf blotch.

22. The method according to claim 15 wherein the composition comprises about 0.038% wt/vol to 0.45% wt/vol of the compound, about 0.05% vol/vol to 4.0% vol/vol of the oil, and water.

23. The method according to claim 15 wherein the compound is applied at a rate of about 0.05 kg/ha to 0.5 kg/ha and the oil is applied at a rate of about 0.1 L/ha to 4.0 L/ha.

* * * * *